United States Patent [19]
Taiariol et al.

[11] Patent Number: 5,017,490
[45] Date of Patent: May 21, 1991

[54] METHOD FOR IN VITRO REPRODUCTION AND GROWTH OF CELLS IN CULTURE MEDIUM

[75] Inventors: Van Taiariol, Redwood City; Robert V. Oakley, Lafayette; Peter Ventura, Daly City, all of Calif.

[73] Assignee: Baxter International Inc., Deerfield, Ill.

[21] Appl. No.: 321,765

[22] Filed: Mar. 10, 1989

[51] Int. Cl.⁵ .............................................. C12N 5/06
[52] U.S. Cl. ........................... 435/240.2; 435/240.23; 435/240.241; 435/240.25; 435/284
[58] Field of Search ......... 435/240.2, 240.23, 240.241, 435/240.25, 243, 284–286, 296, 299–301, 311, 313, 800, 818, 819, 1, 2; 422/102, 101; 604/410; 206/438, 439; 383/2, 37, 102

[56] References Cited

U.S. PATENT DOCUMENTS

| 3,102,082 | 8/1963 | Brewer | 435/301 |
| 3,257,072 | 6/1966 | Reynolds | 604/410 |
| 3,946,780 | 3/1976 | Sellers | 435/313 |
| 4,059,486 | 11/1977 | Tolbert | 435/240.23 |
| 4,132,594 | 1/1979 | Bark et al. | 435/2 |
| 4,507,114 | 3/1985 | Bohman et al. | 604/111 |
| 4,632,244 | 12/1986 | Landau | 206/219 |
| 4,717,668 | 1/1988 | Keilman et al. | 435/296 |

FOREIGN PATENT DOCUMENTS 3248543 7/1983 Fed. Rep. of Germany .
WO8706952 11/1981 PCT Int'l Appl. .
WO8800235 1/1988 PCT Int'l Appl. .

OTHER PUBLICATIONS

"Lifecell" Flask, Product Literature.
Kolanko, W. et al., "Improved Yields of Monoclonal Antibodies in Flexible Plastic Containers", 1987.

Primary Examiner—David L. Lacey
Assistant Examiner—William H. Beisner
Attorney, Agent, or Firm—St. Onge Steward Johnston & Reens

[57] ABSTRACT

Method and apparatus for in vitro culture of cells in culture medium to produce a viable cell mass of cell number greater than the initial cell number, wherein a cell mass of particular cell number is cultured in a first oxygen-permeable culture sub-compartment to an increased cell number, and then aseptically transferred directly from the first sub-compartment to a next serial culture sub-compartment providing additional medium and/or culture space for further growth and reproduction to produce a viable cell mass of still higher cell number. Continued transfers are made, if necessary, to successive serial culture sub-compartment until a viable cell mass of desired cell number is attained, particularly one useful for seeding of a production-scale culture system.

11 Claims, 2 Drawing Sheets

METHOD FOR IN VITRO REPRODUCTION AND GROWTH OF CELLS IN CULTURE MEDIUM

BACKGROUND OF THE INVENTION

This invention relates to the in vitro culture of living cells, such as animal cells, to achieve reproduction and growth of the cells to a desirably high cell number, and more particularly to methods and apparatus for the preparation of high cell number cell masses for seeding production-scale culture systems.

The in vitro culture of animal cells has long been in use for a variety of purposes, and in recent years has received considerable attention and achievement as a means for production and recovery of cell-manufactured proteins of established or potential therapeutic and/or diagnostic utility, be it through culture of naturally-occurring, protein-producing animal cells, or culture of protein-producing hybrids formed from such animal cells, or culture of animal host cells which have been transformed, via recombinant DNA technology, using heterologous genes coding for a particular protein product.

For most such processes, relatively large-scale culture systems are desirable as a means for meeting production demands for the protein and/or for decreasing the per unit production cost of the protein. As is well-known, it is neither economic nor generally even feasible to initiate such culture processes utilizing only a small number of cells. As a consequence, it is routinely necessary to first separately produce a homogeneous cell mass of sufficiently high cell number so as to provide an initial inoculum of cells to the production culture system which insures viability therein and results in economic production of cell-manufactured proteins.

To this end, a small initial charge of cells and an appropriate quantity and type of culture medium are introduced into a suitable small volume vessel such as a tissue culture (T) flask, spinner flask, roller bottle or the like, in the presence of a suitable gaseous environment for providing, e.g., a mixture of oxygen and carbon dioxide to the cells. In this small-scale environment, a mass of low cell number can retain viability and reproduce and grow to a higher cell density until confluency is attained.

If a suitably high cell number can be directly produced in this manner, the cells must then be removed from the flask or bottle and then inoculated, optionally as a suspension in fresh culture medium, into the production culture unit, an operation which can be difficult and time-consuming and, most importantly, must be carried out under strictly sterile conditions lest the entire inoculum be contaminated.

As is more often generally the case, the increase in cell number achieved in the small flask or bottle is not sufficiently great to permit the cells to be directly introduced into the production culture unit, yet the original flask or bottle is too small to accommodate further medium, growth and reproduction. In such circumstances, the cells are transferred to a suitably larger flask or bottle for further introduction of medium and further growth and reproduction to an increased cell number. For many cell lines, a number of such transfers to increasingly larger capacity vessels is needed before a viable cell mass of sufficiently high cell number is achieved which can be inoculated into the production culture unit.

With each transfer of a cell mass from one preliminary growth vessel to another and eventually to the production culture unit, the risk of contamination of the inoculum exists. If such contamination occurs, say, in the later stages of transfer, the entire process must be repeated from the beginning thereby greatly increasing the time and cost involved in obtaining a suitable inoculum for the production culture unit and greatly increasing the time and cost involved in culturing cells for recovery of their manufactured proteins.

The primary object of the present invention is to provide a means for growing up cells to a cell number suitable for introduction into a production culture system, under conditions which provide a sufficiently small-scale starting environment for insuring viability of the cells, an increasingly larger-scale environment as necessary, and a means for eventual introduction of the high cell number mass to a culture unit, without risk of transfer contamination and in an economic and time-conserving manner.

SUMMARY OF THE INVENTION

These and other objects as will be apparent are achieved by the provision of an animal cell culture process and apparatus in which there is provided at least two serial culture sub-compartments, each formed from a flexible material which is compatible with cell culture (i.e., biologically inert) and gas (i.e., oxygen, carbondioxide)-permeable, each sub-compartment being in at least latent direct or indirect fluid communication with the next serial sub-compartment such that the contents of the sub-compartment can be transferred to the next serial sub-compartment without need for invasion of the overall system or the sub-compartments.

In operation, an initial charge of cells (e.g., from an established cell line) and a suitable amount of appropriate culture medium are aseptically introduced into the first sub-compartment of the series. The series of sub-compartments is maintained in a suitable gaseous environment (e.g., in an incubator) which, by virtue of the gas permeability of the sub-compartment material, is effective to provide within each of the sub-compartments the gaseous environment required for cell viability, growth and reproduction.

Generally, the conditions present in the first culture sub-compartment (e.g., amount of medium and, optionally, available surface area and/or volume) are such as to provide optimum conditions for encouraging the small initial charge of cells to grow and multiply such that a mass of larger cell number is produced. When the limit of practical cell growth and viability has been reached in this first sub-compartment, the contents thereof (i.e., cells, medium) are transferred into the next serial sub-compartment. In this next sub-compartment, by reason of additional medium therein and/or greater available surface area and/or volume, the cell mass from the first sub-compartment is provided with the conditions required for further increase in cell number with retained viability. This transfer from one serial sub-compartment to the next can be continued as necessary with successive sub-compartments until a cell mass of suitably high cell number for seeding a production-scale culture system is obtained, which seeding can be performed aseptically directly from the last culture sub-chamber.

In accordance with the invention, the transfer of contents from one culture sub-compartment to the next is effected aseptically without need for opening the compartments to the environment or for undergoing elaborate precautions to prevent such exposure. In one embodiment of the invention, the sub-compartments are connected by suitable tubing through which contents from one sub-compartment can be transferred to the next serial sub-compartment, while in another embodiment, the sub-compartments are formed by appropriate closure or clamping of a unitary compartment, whereby removal of the closure means results in formation of a larger serial sub-compartment into which the contents of the prior sub-compartment are transferred.

DETAILED DESCRIPTION OF THE INVENTION

Figure 1:
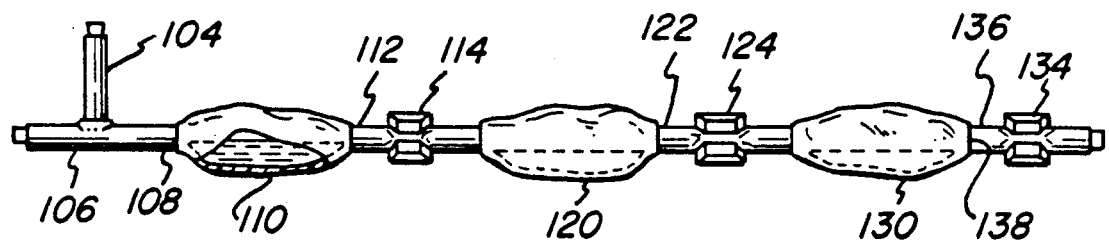
FIG. 1 shows a side view of a three sub-compartment culture system according to one embodiment of the invention.

In accordance with a first embodiment of the invention, illustrated in FIG. 1, a culture system is provided which consists, for illustration purposes, of three serial culture sub-compartments 110, 120 and 130, interconnected by tubing segments 112 and 122. Sub-compartment 110, chosen as the initial sub-compartment in this illustration, also has associated with it an entry port 108 in communication with inlet tube 106 through which cells and culture medium can be introduced, tube 106 preferably having a separate seed port 104 for inoculation of cells. Compartment 130 has associated with it an exit port 138 in communication with outlet tube 136 for withdrawing cells and medium therefrom.

The material used to form tubing segments 112 and 122 (and also, preferably, tubing segments 104, 106 and 136) is a biologically inert, sterilizable material such as silicone rubber which can be compressed (e.g., with appropriately placed clamps 114 and 124) to prevent liquid communication between sub-compartments 110, 120 and 130 until desired. As such, the culture sub-compartments are in latent indirect liquid communication when the clamping or other compressive means are in place.

The material forming the culture sub-compartments 110, 120 and 130 is chosen to be sufficiently flexible so that the contents (cells and medium) in the sub-compartment can be emptied therefrom by external manipulation of the sub-compartment, e.g., by squeezing, and also to facilitate dislodging of cells from sub-compartment surfaces if anchorage-dependent animal cells are involved.

The enclosure-forming material for the sub-compartments also is chosen so as to be sterilizable (e.g., by irradiation, autoclaving or the like). Finally, the enclosure-forming material is chosen to be permeable to a gaseous atmosphere within which the culture system will be arranged and as typically will be employed in animal cell culture (e.g., 95% oxygen, 5% $CO_2$). Preferably, the enclosure-forming material is chosen so as to have a very high permeability to these gases per unit surface area. These requirements can be met by a number of flexible plastic and rubber-like materials such as silicone rubber, fluoro-ethylene-propylene copolymer, and plastics formed of polypropylene and a block copolymer having a central block of a rubber olefin polymer of ethylene units and terminal blocks of polystyrene and polyethylenevinyl acetate softening agent (see U.S. Pat. No. 4,717,668). Preferred in the present invention is the use of silicone rubber sheeting material.

The sub-compartments 110, 120 and 130 can each be of the same size (internal surface area and/or volume) or can be successively larger if desired, it being recognized that the flexible nature thereof permits of effective expansion of culture area and/or volume upon increase of the quantity of contents therein.

In the preferred operation of this embodiment, each of sub-compartments 110, 120 and 130 is provided with a quantity of culture medium, the entire system sterilized, and arranged in an incubator having the appropriate gaseous environment. The tubing segments are clamped at 114, 124 and 134, and an initial charge of cells from a cell line introduced into sub-compartment 110 through tubes 104 and 106 (which can then be clamped if desired; alternatively, tube 106 can be provided with a plug or septum through which cells can be injected). The cells grow and multiply in sub-compartment 110 in the presence of the suitable (e.g., small) amount of culture medium therein and in the relatively small area/volume of sub-compartment 110 occupied by the cells and medium, all of which optimizes growth and viability of the initially relatively small number of cells. As the cell number increases and nutrients in the medium are consumed, the cells in sub-compartment 110 eventually reach confluency and require additional medium and space to further multiply. At this stage, clamp 114 is removed and the bag-like sub-compartment 110 is then manipulated (e.g., by squeezing) to pump or transfer its contents through tube segment 112 and into sub-compartment 120 where additional medium and area (albeit still limited so as to provide optimum conditions for viability and growth) exist. If desired, tube segment 112 can be re-clamped after the transfer. As in sub-compartment 110, the cells in sub-compartment 120 grow to confluency and are then transferred through tube segment 122 (after removal of clamp 124) to sub-compartment 130 which provides further medium and area for continued increase in cell number with retained viability. Finally, when a cell mass of cell number suitable for inoculation into a production-scale culture unit is attained, the cells and medium from sub-compartment 130 are transferred through tube 136 to an appropriate inlet to the production unit.

In an alternate embodiment using the system of FIG. 1, culture medium need not be initially provided in each of the sub-compartments, but can be added (or supplemented) through appropriate inlets to each sub-compartment. This mode of operation is not as preferable, however, as having culture medium pre-loaded into each sub-compartment since the need to invade the compartments to effect medium loading could risk contamination.

As is apparent, a sub-compartmented culture system of this type can be pre-manufactured containing any number of sub-compartments and connecting tube segments. Where sufficient cell number is attained using less than all the pre-manufactured and arranged sub-compartments, it is possible to then either by-pass the remaining sub-compartments (e.g., by disconnecting them) and proceed directly to an inoculation inlet in a production culture unit, or, alternatively to proceed through the remaining sub-compartments to the ultimate outlet of the system but without need for effecting culturing in the unneeded sub-compartments.

Figure 2:
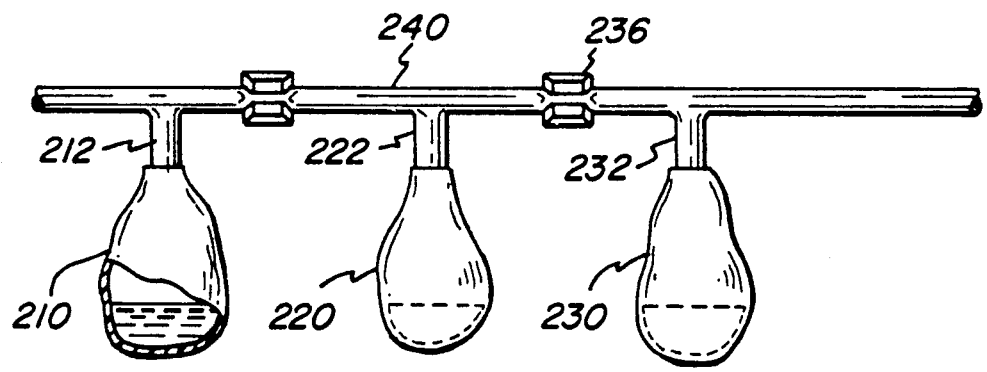
FIG. 2 shows a side view of a three sub-compartment culture system according to another embodiment of the invention.

In this latter regard, the culture system of FIG. 2 has advantage. Here, the bag-like sub-compartments 210, 220 and 230, pre-filled with culture medium, are in latent indirect liquid communication by virtue of tube segments 212, 222 and 232 which in turn communicate with common tube segment 240, all of which segments can be suitably clamped. As in the system of FIG. 1, cells introduced into sub-compartment 210 grow and multiply in the medium therein and can then be transferred (e.g., by squeezing of the sub-compartment) to sub-compartment 220 through tubes 212, 240 and 222 with appropriate clamping (e.g., at 236). If a suitable cell number has been attained in sub-compartment 220, sub-compartment 230 is readily by-passed by clamping of tube segment 232 and squeezing the contents of compartment 220 so that they enter tube 240 for exit from the system.

A preferred form of the invention is shown in FIGS. 3A-3C and FIG. 4, where the sub-compartments are formed by suitable clamping of a unitary bag-like enclosure, such that the sub-compartments are in latent direct liquid communication. Preferably, each sub-compartment for culture consists of itself and any previous sub-compartment; however, in an alternative embodiment, albeit less preferred, each sub-compartment can be maintained as discrete throughout the process.

For preferred operation, a culture chamber, generally designated by the numeral 310, is comprised of a length of biologically inert, flexible, gas-permeable material 320 arranged in a manner to form a bag-like enclosure 322 (see FIG. 3C for initially-manufactured configuration) constituting an overall, total culture compartment.

The enclosure-forming material is sufficiently flexible such that external segmenting means 324 can be employed to subdivide the overall culture compartment into one or more culture sub-compartments (e.g., 326, 328, 330) which, by reason of the applied segmenting means, are isolated one from the other so that little if any liquid communication exists therebetween when the segmenting means are in place. As before, the enclosure-forming material 320 also is chosen so as to be sterilizable (e.g., by irradiation, autoclaving or the like) and permeable to a gaseous atmosphere within which the culture chamber will be arranged and as typically will be employed in animal cell culture.

Figure 3A:
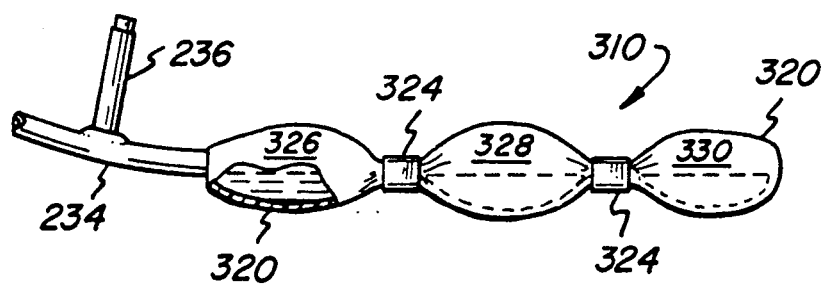
FIGS. 3A, 3B and 3C show a side view of a culture system according to a preferred embodiment of the invention, where a unitary enclosure is divided into three sub-compartments, in its successive stages of expansion to permit and accommodate cell reproduction and growth to a cell mass of suitably high cell number.
Figure 3B:
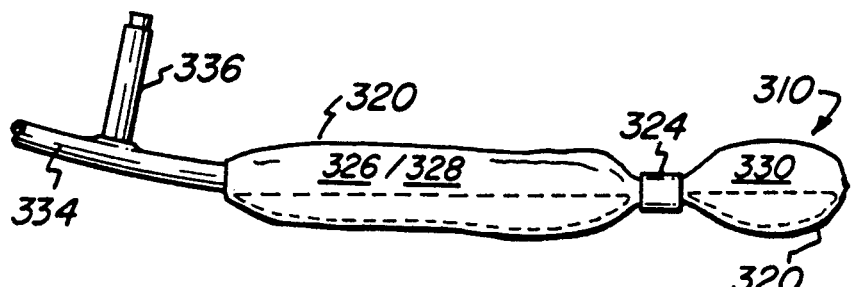
Figure 3C:
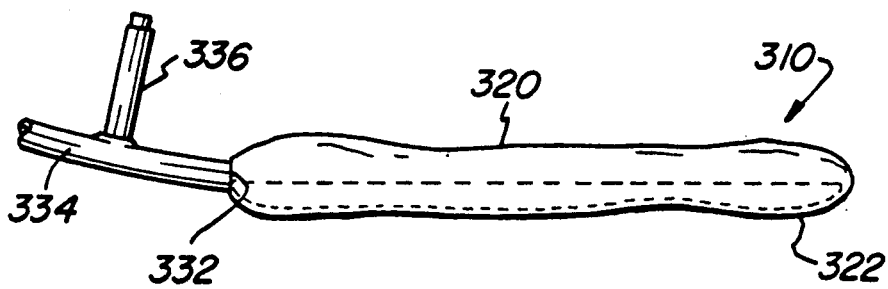
Figure 4:
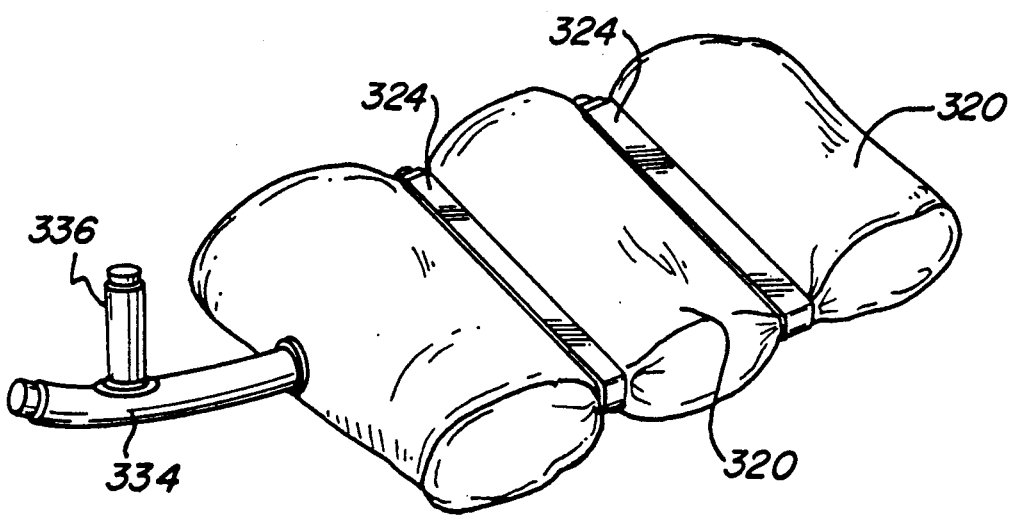
FIG. 4 is a perspective view of the culture system of FIG. 3A.

As shown in the FIGS. 3A, 3B and 3C, the total culture compartment 322 is provided with an open port 332 in communication with a tube 334 through which cells and culture medium can be introduced, tube 334 preferably having a separate seed port 336 for inoculation of cells. Tube 334 also can be used for withdrawing the final cell mass and medium from the culture compartment, e.g., for aseptic introduction into a production culture unit; alternatively, separate withdrawal means can be provided elsewhere.

Isolation clamps 324 or other suitable segmenting means are applied at one or more appropriate points along the external surfaces of the total culture compartment 322 to compress the enclosure-forming material against itself at these points and thus divide the culture compartment into two or more culture sub-compartments (e.g., 326, 328 and 330) with sufficient external pressure so as to substantially (and preferably, entirely) prevent culture medium and cells from passing between sub-compartments.

As shown for purpose of illustration in FIG. 3A, two isolation clamps 324 are used to form three initial culture sub-compartments 326, 328 and 330. Depending upon the initial cell number of the available cell stock, the growth characteristics of the cells, and the needed final cell number, any appropriate number of culture sub-compartments can be provided, each sub-compartment can be arranged to be of any suitable size (e.g., surface area, volume), and each sub-compartment can be the same size or a size different from that of the preceding sub-compartment. In a typical culture chamber according to the invention as illustrated in FIG. 3A, the sub-compartments 26, 28 and 30 have approximate volumes of 50 ml., 500 ml. and 1000 ml.

In operation, the culture chamber, as configured in FIG. 3A, is sterilized (the ends of tubes 334 and 336 being closed off with clamps or rubber plugs), arranged in a suitable enclosure providing the requisite gaseous environment, and then seeded with an initial suspension of cells and culture medium, as by injection through a plug or septum in tube 336. In this manner, the cells and culture medium are confined within sub-compartment 326 for initial growth and reproduction to produce a higher cell number within the sub-compartment. As the cell number increases and nutrients in the culture medium are consumed, the cells eventually reach confluency. At this stage, the isolation clamp 324 separating sub-compartment 326 from sub-compartment 328 is released so that these sub-compartments enter into liquid communication and merge into a single larger culture sub-compartment 326/328 (FIG. 3B). With access now to culture medium initially present in sub-compartment 328 (and/or with addition of increased medium via inlet 334), the larger sub-compartment 326/328 now available to the cells enables them to further increase in cell number. When confluency is reached, the final isolation clamp 324 is removed so as to permit sub-compartment 330 to enter into liquid communication with previously-merged sub-compartment 326/328 to form a new and larger culture space defined by the overall culture compartment 322 (FIG. 3C). Again with access to and/or addition of an increased volume of fresh medium, the larger culture space available to the cells and medium enables the cells to further increase in cell number, eventually reaching a cell number suitable for introduction of the cells into a production culture unit. This preferably is accomplished by forming a sterile connection between tube 334 and an inlet to the production culture unit and then transferring the cells and medium from culture compartment 322, through the sterile connection, to the production culture unit.

As is apparent from the foregoing description, the present invention provides a means for effecting simple and economic transfer of cells and medium into either progressively larger culture spaces and/or culture spaces making available additional fresh medium for continued increase in cell number without having to invade the sterility of the system and without risk of contamination during transfer, as can occur, for example, in transfers between one flask or roller bottle to another unless elaborate and expensive devices and procedures are employed. More importantly, should any contamination have occurred it can be ascertained early in the process. For example, with reference for illustration purposes to the embodiment of FIG. 3, a useful expedient is to remove a small portion of seed port 336 at just about the time that sub-compartment 326 has been merged into sub-compartment 328, and to use the liquid and cells in that removed portion (which is in liquid communication with the culture sub-compartment) for contamination analysis. If for some reason the culture is contaminated, the process can be terminated at that early point before substantial time and media has been expended in continued growth of the cells. If no contamination is found, no further opportunity for contamination is likely to occur since the subsequent transfers from one sub-compartment to the next are effected without invasion of the sterile system.

The culture system of FIG. 3 can be fabricated to be of any desired overall size and configuration, particularly since the segmenting means can be arranged at any desired areas about the enclosure surface to form sub-compartments of any desired size irrespective of the overall size of the culture chamber. Where the sub-compartments are to be used individually (i.e., not merged into a larger serial sub-compartment), it is preferred that each sub-compartment be progressively larger than the next. Where the system is operated by merging the previous sub-compartment into the next succeeding one, the original individual sub-compartments can all be the same or different sizes, and need not necessarily be progressively larger throughout the overall system.

For the embodiments of FIGS. 1 and 2, it is generally preferred, but not mandatory, that each successive sub-compartment have a larger volumetric capacity than the previous one.

In a typical system for culture using the invention, each sub-compartment contains about one liter of culture medium, and cells are seeded into the first compartment at a cell density of about $5-20 \times 10^4$ cells/ml (thus, $5-20 \times 10^7$ cells in the first compartment). After about 48–96 hours propagation, the cell density has increased to $5-20 \times 10^5$ cells/ml (thus, $5-20 \times 10^8$ cells). Thereafter, the means isolating the first and second sub-compartments is removed, and the contents of the first sub-compartment then transferred to the second sub-compartment for further propagation, now having a starting cell density in the sub-compartment of $5-20 \times 10^8$ cells in two liters of medium. Subsequent propagation and transfer into the next successive sub-compartment (generally every 24–72 hours) is conducted until a suitable cell number is achieved for inoculation into a production culture system.

The thickness of enclosure-forming material used to define the culture sub-compartments can be any thickness suitable for achieving the requisite flexibility and gas-permeability of the material. For silicone rubber sheet material, a thickness between about 0.003 to 0.01 inches is suitable.

The culture chamber of the present invention is particularly useful for suspension culture of cells which do not need to attach to surfaces in order to grow and reproduce, but also can be employed using adherent cells. In such cases, the flexible nature of the enclosure-forming material makes it possible to dislodge cells from its inner surfaces by tapping or other manipulation of the material so that the cells will dislodge and then reattach along the larger surface presented to them in a subsequent merged culture sub-compartment. Where this expedient is not effective, resort generally will be had to trypsination to dislodge the cells for reattachment to expanded growth surfaces.

As previously noted, the present invention finds its greatest utility in growing up of an initial seed stock to a sufficiently high cell number so as to permit the cells to be inoculated into a production culture system at a cell number which is most effective for the production system. In this way, the cell line is given its best chance for viability in the environment of the production culture system and less time is required to be devoted in the production system to expansion of the cell mass to numbers optimum for production of proteins. Alternatively, however, the culture system of the invention can be used as a small-scale production culture per se in those situations where only small quantities of cell-secreted proteins are required, and also can be used to study the growth characteristics of particular cell lines and/or the effect of various parameters (e.g., media, gas concentration) on growth, reproduction, or secretion of particular cell lines. In each instance, the culture system of the invention permits expansion of the cell number to the point needed for production or study or observation without need for resorting to one or more vessel to vessel transfers.

Although the invention has been described with reference to particular embodiments, materials of construction, operating parameters and the like, it will be understood that these are presented as being illustrative of the invention and its fundamental features, and that numerous modifications can be made without departing from the spirit and scope of the invention as defined in the appended claims.

What is claimed is:

1. A method for the in vitro culturing of animal cells in a culture medium to produce, from an initial viable cell mass of particular cell number, a viable cell mass of larger cell number, comprising the steps of:
    (a) providing a series of animal cell culture sub-compartments, each sub-compartment comprising a culture space for animal cells and for culture medium, defined by a flexible material permeable to oxygen, said series further comprising regulating means, operable external of the culture space, for variably permitting or precluding liquid communication between any given sub-compartment in said series and at least a next serial sub-compartment in said series;
    (b) arranging said series of animal cell culture sub-compartments in a controlled gaseous environment, comprising oxygen, suitable for in vitro animal cell culture;
    (c) introducing culture medium and a viable cell mass of particular cell number into a first culture sub-compartment of said series, isolated by said regulating means from liquid communication with any other sub-compartment of said series;
    (d) maintaining in said first culture sub-compartment conditions effective to cause said viable cell mass therein to increase in cell number
    (e) thereafter establishing liquid communication, by said regulating means, between said first culture sub-compartment and a next serial culture sub-compartment of said series provided with at least additional culture medium or culture space, and transferring said viable cell mass of increased cell number, and culture medium, from said first culture sub-compartment to said next serial culture sub-compartment;

(f) maintaining in said next serial sub-compartment conditions effective to cause said cell mass therein to further increase in cell number; and (g) withdrawing from said next serial culture sub-compartment said viable cell mass of further increased cell number.

2. A method according to claim 1 wherein each of the culture sub-compartments of said series has a liquid inlet and a liquid outlet; wherein said liquid outlet for a given culture sub-compartment is connected by a conduit to the inlet of a next serial sub-compartment of said series; and wherein said regulating means is arranged at said conduit.

3. A method according to claim 2 wherein said conduit comprises compressible material, and wherein said regulating means comprises a removable compression clamp about the periphery of said compressible material.

4. A method according to claim 1 wherein said series of culture sub-compartments further comprises an elongate common conduit; and wherein each said sub-compartment further comprises a tube segment, one end of which is in liquid communication with the culture space of said sub-compartment and the other end of which is in liquid communication with said elongate common conduit.

5. A method according to claim 4 wherein said regulating means is arranged at one or more of said tube segments.

6. A method according to claim 4 wherein said regulating means is arranged a one or more locations along said elongate common conduit.

7. A method according to claim 4 wherein said elongate common conduit and said tube segments comprise compressible material, and wherein said regulating means comprises a removable compression clamp about the periphery of said compressible material.

8. A method according to claim 1 wherein said culture sub-compartments of said series comprise segmented portions of a single bag-like enclosure of said flexible material.

9. A method according to claim 8 wherein said segmented portions are formed by removable external segmenting means applied at one or more locations along said single bag-like enclosure, and wherein said regulating means comprise said removable external segmenting means.

10. A method for the in vitro culturing of animal cells in a culture medium to produce, from an initial viable cell mass of particular cell number, a viable cell mass of larger cell number, comprising the steps of:

(a) providing an enclosed overall culture compartment of defined surface area and volume comprising a flexible oxygen-permeable material, said overall culture compartment being divided into two or more culture sub-compartments by removal segmenting means displaced about the periphery of the enclosed culture compartment;

(b) arranging said overall culture compartment in a controlled gaseous environment, comprising oxygen, suitable for in vitro cell culture;

(c) introducing culture medium and a viable cell mass of particular cell number into a first of said sub-compartments;

(d) maintaining in said first sub-compartment conditions effective to cause said viable cell mass therein to increase in cell number;

(e) thereafter removing said segmenting means between said first sub-compartment and a next serial sub-compartment, whereby there is produced a united larger culture space, comprised of said first sub-compartment and said next serial sub-compartment, for culture of the cells from said first sub-compartment; and (f) maintaining in said united larger culture space conditions effective to cause the cell mass therein to further increase in cell number.

11. A method according to claim 10 wherein each of said culture sub-compartments has culture medium prearranged therein.

* * * * *